US005874621A

United States Patent [19]
Eller et al.

[11] Patent Number: 5,874,621
[45] Date of Patent: Feb. 23, 1999

[54] PREPARATION OF AMINES FROM OLEFINS OVER NU-85 ZEOLITES

[75] Inventors: Karsten Eller, Ludwigshafen; Rudolf Kummer, Frankenthal; Matthias Dernbach, Eppelheim; Hans-Jürgen Lützel, Böhl-Iggelheim, all of Germany

[73] Assignee: BASF Aktiengesellschaft, Ludwigshafen, Germany

[21] Appl. No.: 22,676

[22] Filed: Feb. 12, 1998

[30] Foreign Application Priority Data

Feb. 25, 1997 [DE] Germany ................. 197 07 386.7

[51] Int. Cl.⁶ ................................. C07C 209/60
[52] U.S. Cl. ............................. 564/445; 564/485
[58] Field of Search ..................... 564/485, 445

[56] References Cited

U.S. PATENT DOCUMENTS

| | | |
|---|---|---|
| 4,375,002 | 2/1983 | Peterson et al. |
| 4,536,602 | 8/1985 | Deeba |
| 4,929,758 | 5/1990 | Taglieber et al. |
| 5,648,546 | 7/1997 | Bergfeld et al. ............ 564/485 |

FOREIGN PATENT DOCUMENTS

| | | |
|---|---|---|
| 2 092 964 | 6/1994 | Canada |
| 101 921 | 3/1984 | European Pat. Off. |
| 132 736 | 2/1985 | European Pat. Off. |
| 133 938 | 3/1985 | European Pat. Off. |
| 305 564 | 3/1989 | European Pat. Off. |
| 431 451 | 6/1991 | European Pat. Off. |
| 462 745 | 2/1996 | European Pat. Off. |
| 42 06 992 | 9/1993 | Germany |

OTHER PUBLICATIONS

Jr. of Molecular Catlysis, 49 (1989)235–259.
Method of solution and structure of 3 novel . . . 389–398,
Shannon Studies in Surface Sci. and Catalysis, vol. 37, 1988.

Primary Examiner—Brian M. Burn
Attorney, Agent, or Firm—Keil & Weinkauf

[57] ABSTRACT

Amines of the general formula I

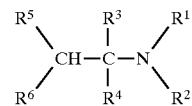

where $R^1$, $R^2$, $R^3$, $R^4$, $R^5$ and $R^6$: are each hydrogen, $C_1$–$C_{20}$-alkyl, $C_2$–$C_{20}$-alkenyl, $C_2$–$C_{20}$-alkynyl, $C_3$–$C_{20}$-cycloalkyl, $C_4$–$C_{20}$-alkylcycloalkyl, $C_4$–$C_{20}$-cycloalkylalkyl, aryl, $C_7$–$C_{20}$-alkylaryl or $C_7$–$C_{20}$-aralkyl, $R_1$ and $R^2$ together are a saturated or unsaturated $C_3$–$C_9$-alkylene chain and $R^3$ or $R^5$ is $C_{21}$–$C_{200}$-alkyl or $C_{21}$–$C_{200}$-alkenyl or $R^3$ and $R^5$ together are a $C_2$–$C_{12}$-alkylene chain, are prepared by reacting an olefin of the general formula II

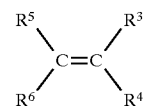

where $R^3$, $R^4$, $R^5$ and $R^6$ have the abovementioned meanings, with ammonia or a primary or secondary amine of the general formula III

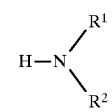

where $R^1$ and $R^2$ have the abovementioned meanings, at from 200°0 to 350° C. and from 100 to 300 bar in the presence of a heterogeneous catalyst, wherein the heterogeneous catalyst used is an NU-85 zeolite.

11 Claims, No Drawings

PREPARATION OF AMINES FROM OLEFINS OVER NU-85 ZEOLITES

The present invention relates to a process for the preparation of amines by reacting ammonia or primary or secondary amines with olefins at elevated temperatures and superatmospheric pressure in the presence of NU-85 zeolites.

An overview of the methods for aminating olefins is given in Functionalization of Alkenes: Catalytic Amination of Monoolefins, J. J. Brunet et al., J. Mol. Catal. 49 (1989), 235–259.

There are in principle two catalysis mechanisms. The olefin is coordinated via a metal complex. This activated species can be attacked by the nucleophilic amine and can form a more highly aminated product. The amine can be chemisorbed at acid centers or at metal centers (via metal amides) and, in this activated form, can be reacted with the olefin.

Suitable catalysts are zeolites. They are distinguished by a large number of catalytically actives centers in combination with a large surface area. The zeolites described differ in type and in the aftertreatment (for example, thermal treatment, dealumination, acid treatment, metal ion exchange, etc.). Examples of these appear in U.S. Pat. No. 4,375,002, U.S. Pat. No. 4,536,602, EP-A-305 564, EP-A-101 921 and DE-A-42 06 992.

EP-A-133 938, EP-A-431 451 and EP-A-132 736 disclose processes in which borosilicate, gallosilicate, aluminosilicate and ferrosilicate zeolites are used for the preparation of amines from olefins and indicate the possibility of doping these zeolites with alkali metals, alkaline earth metals and transition metals.

CA-A-2 092 964 discloses a process for the preparation of amines from olefins, using BETA zeolites, which are defined as crystalline aluminosilicates having a certain composition and a pore size of more than 5 Å. Metal- or halogen-modified beta-zeolites are preferably used.

All processes for the synthesis of amines from olefins over these catalysts are distinguished by a low amine yield or low space-time yield or lead to rapid deactivation of the catalysts.

It is an object of the present invention to remedy these disadvantages.

We have found that this object is achieved by a novel and improved process for the preparation of amines of the general formula I

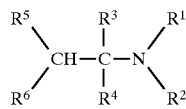

where $R^1$, $R^2$, $R^3$, $R^4$, $R^5$ and $R^6$: are each hydrogen, $C_1$–$C_{20}$-alkyl, $C_2$–$C_{20}$-alkenyl, $C_2$–$C_{20}$-alkynyl, $C_3$–$C_{20}$-cycloalkyl, $C_4$–$C_{20}$-alkylcycloalkyl, $C_4$–$C_{20}$-cycloalkylalkyl, aryl, $C_7$–$C_{20}$-alkylaryl or $C_7$–$C_{20}$-aralkyl, $R^1$ and $R^2$ together are a saturated or unsaturated $C_3$–$C_9$-alkylene chain and $R^3$ or $R^5$ is $C_{21}$–$C_{200}$-alkyl or $C_{21}$–$C_{200}$-alkenyl or $R^3$ and $R^5$ together are a $C_2$–$C_{12}$-alkylene chain, by reacting an olefin of the general formula II

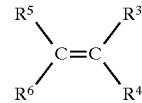

where $R^3$, $R^4$, $R^5$ and $R^6$ have the abovementioned meanings, with ammonia or a primary or secondary amine of the general formula III

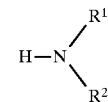

where $R^1$ and $R^2$ have the abovementioned meanings, at from 200° to 350° C. and from 100 to 300 bar in the presence of a heterogeneous catalyst, wherein the heterogeneous catalyst used is an NU-85 zeolite.

The novel process can be carried out as follows:

The olefin II and ammonia or the primary or secondary amine III can be reacted at from 200° to 350° C., preferably from 220° to 330° C., particularly preferably from 230° to 320° C., and from 100 to 300, preferably from 120 to 300, particularly preferably from 140 to 290, bar in the presence of an NU-85 zeolite as the catalyst, for example in a pressure-resistant reactor, and preferably the amine obtained is isolated and the unconverted starting materials are recycled.

The present process gives a very good yield in combination with high selectivity and high space-time yield. Moreover, the deactivation of the catalyst has been suppressed.

The novel process is distinguised by the fact that, even with a small excess of ammonia or amine, a high selectivity with respect to the desired reaction product is achieved and the dimerization and/or oligomerization of the olefin used is avoided.

In one embodiment of this process, ammonia and/or amines III, mixed with the olefin II in a molar ratio of from 1:1 to 5:1, are fed to a fixed-bed reactor and reacted at from 100 to 300 bar and from 200° to 350° C. in the gas phase or in the supercritical state.

The desired product can be obtained from the reacted mixture with the aid of known methods, for example distillation or extraction, and if necessary brought to the desired purity by means of further separation operations. The unconverted starting materials are as a rule preferably recycled to the reactor.

Mono- or polyunsaturated olefins II, in particular those of 2 to 10 carbon atoms, or mixtures thereof and polyolefins may be used as starting materials. Owing to the small tendency to polymerization, monoolefins are more suitable than di- and polyolefins, but these too can be selectively reacted with the aid of a larger excess of ammonia or of amine. The position of the equilibrium and hence the conversion to the desired amine is very highly dependent on the reaction pressure chosen. High pressure favors the adduct, but for technical and economic reasons the pressure range up to 300 bar is in general the optimum. The selectivity of the reaction is influenced to a high degree by the temperature, as well as by parameters such as ammonia/amine excess and catalyst. Although the reaction rate of the addition reaction increases sharply with increasing temperature, competing crack and recombination reactions of the olefin are simultaneously promoted. Moreover, a temperature increase is disadvantageous from the thermodynamic point of view. The optimum temperature with regard to conversion and selectivity is dependent on the constitution of the olefin, of the amine used and of the catalyst and is in general from 200° to 350° C.

Suitable catalysts for the amination of olefins are NU-85 zeolites, which are disclosed in EP-A-462 745. In terms of the structure, they are mixed crystals comprising NU-87 and EU-1 but have a multidimensional channel system (Shannon, Proc. 9th Int. Zeolite Conf. (1992) 389), while EU-1 (EUO) is a unidimensional ten-ring zeolite, ie. a pentasil. All mixed crystals between the pure EU-1 and the pure NU-87 (NES) are referred to as NU-85.

In addition to the NU-85 zeolites containing aluminum as a trivalent element in the $SiO_2$ matrix, as described, for example, in EP-A-462 745, other elements are also possible for the purposes of this application if acidic centers are created as a result of their incorporation. This is the case, for example, with boron zeolites, iron zeolites or gallium zeolites. The molar ratio of $SiO_2$ to the oxides of the trivalent elements, ie. the modulus $SiO_2/M_2O_3$ (m=Al, B, Ga or Fe), may vary from virtually infinity to a few multiples of ten, depending on the zeolite class. By varying the modulus, the activity of the zeolite can be tailored to the particular amination reaction, in order to obtain optimum results.

Instead of the trivalent element, silicon can also be isomorphically substituted by other tetravalent elements, for example Ge, Ti or Sn.

In addition to the classical $SiO_2$-based zeolites, it is also possible to realize analogous structures based on aluminum phosphates, ie. the AlPOs. If these contain aluminum and phosphorus in a ratio greater than 1, they too are acidic and can be used for the purposes of the present invention. If some of the phosphorus and/or simultaneously aluminum and phosphorus is or are replaced by silicon, the SAPOs are obtained, which are likewise acidic. If, in addition to aluminum and phosphorus, various metal ions, for example Li, B, Be, Mg, Mn, Fe, Co, Zn, Ga, Ge or As, are also present, the term MeAPOs is used, or, with the simultaneous presence of silicon, the term MeAPSOs, in which the negative charge of the $Me_aAl_bP_cSi_dO_e$ framework is compensated in each case by cations. The novel catalysts include all such moelcular sieves having the NU-85 structure.

The novel NU-85 zeolites may be molded as such or with a binder in a weight ratio of from 98:2 to 40:60 to give extrudates or pellets. Suitable binders are various aluminas, preferably boehmite, amorphous aluminosilicates having an $SiO_2/Al_2O_3$ ratio of from 25:75 to 95:5, silica, preferably finely divided $SiO_2$, mixtures of finely divided $SiO_2$ and finely divided $Al_2O_3$, finely divided $TiO_2$ and clays. After molding, the extrudates or pellets are advantageously dried at 110° C. for 16 hours, it also being possible to carry out the calcination directly in the amination reactor.

The novel NU-85 zeolite catalysts may be modified in various ways in order to increase the selectivity, the time-on-stream and the number of possible regenerations.

In one method for modifying the catalyst, the unmolded or the molded zeolites can be subjected to ion exchange or doped with alkali metals, such as Na and K, alkaline earth metals, such as Ca or Mg, earth metals, such as Tl, transition metals, eg. Ti, Zr, Mn, Fe, Mo, Cu, Zn or Cr, noble metals and/or rare earth metals, eg. La, Ce or Y.

In an advantageous embodiment, the molded novel NU-85 zeolites are intially taken in a flow tube and, for example, a halide, an acetate, an oxalate, a citrate or a nitrate of the metals described above, in dissolved form, is passed over said zeolites at from 20° to 100° C. Ion exchange of this type can be carried out, for example, on the hydrogen, ammonium and alkali metal form of the novel NU-85 zeolites.

A further possibility for applying metals to the novel NU-85 zeolites comprises impregnating the material, for example with a halide, an acetate, an oxalate, a citrate, a nitrate or an oxide of the metals described above, in aqueous or alcoholic solution.

Both ion exchange and impregnation may be followed by drying and, if desired, repeated calcination. In the case of metal-doped NU-85 zeolites, an aftertreatment with hydrogen and/or with steam may be advantageous.

A further possible method for modification comprises subjecting the novel NU-85 zeolites, in molded or unmolded form, to a treatment with acids, such as hydrochloric acid (HCl), hydrofluoric acid (HF), sulfuric acid ($H_2SO_4$), phosphoric acid ($H_3PO_4$), oxalic acid ($HO_2C—CO_2H$) or mixtures thereof.

In a particular embodiment, the novel NU-85 zeolites are treated, before being molded, with one of the stated 0.001 to 2N, preferably 0.05 to 0.5N, acids for from 1 to 100 hours under reflux. The product is filtered off and washed and then, as a rule, dried at from 100° to 160° C. and calcined at from 200° to 600° C. A further particular embodiment comprises an acid treatment of the novel NU-85 zeolites after they have been molded with a binder. Here, the novel zeolite is treated with a 3–25%, in particular 12–20%, strength acid, as a rule for from 1 to 3 hours at from 60° to 80° C., then washed thoroughly, dried at from 100° to 160° C. and calcined at from 200° to 600° C. Here too, the calcination can be carried out directly in the amination reactor.

A possible method for modification comprises an exchange with ammonium salts, for example with $NH_4Cl$, or with mono-, di- or polyamines. Here, the zeolite molded with a binder is subjected to exchange with from 10 to 25%, preferably 20%, strength $NH_4Cl$ solution, as a rule at from 60° to 80° C., continuously for 2 hours in zeolite/ammonium chloride solution in a weight ratio of 1:15 and is then dried at from 100° to 120° C.

A further modification which can be carried out on the novel zeolites is dealumination in the case of aluminum zeolites, where some of the aluminum atoms are replaced by silicon or the aluminum content of the zeolite is reduced, for example by hydrothermal treatment. A hydrothermal dealumination is advantageously followed by an extraction with acids or complexing agents, in order to remove non-lattice aluminum formed. Replacement of aluminum with silicon can be effected, for example, with the aid of $(NH_4)_2SiF_6$ or $SiCl_4$. Examples of dealumination of Y-zeolites are to be found in Corma et al., Stud. Surf. Sci. Catal. 37 (1987), 495–503. Correspondingly, with other trivalent oxides the modulus can be increased if some of the boron, of the iron or of the gallium is extracted or is replaced with silicon.

For the amination of the olefins, the catalysts can be used in the form of extrudates having diameters of, for example, from 1 to 4 mm, as beads or as pellets having, for example, diameters of from 3 to 5 mm. Other formed structures are also possible.

A fluidizable material having a size of from 0.1 to 0.8 mm can be obtained by milling and sieving the catalyst, which, for example, has been molded into extrudates.

In the compounds I, II and III,
$R^1$, $R^2$, $R^3$, $R^4$, $R^5$ and $R^6$ are each
hydrogen,
$C_1$–$C_{20}$-alkyl, preferably $C_1$–$C_{12}$-alkyl, particularly preferably $C_1$–$C_8$-alkyl such as methyl, ethyl, n-propyl, isopropyl, n-butyl, isobutyl, sec-butyl, tert-butyl, n-pentyl, isopentyl, n-hexyl, isohexyl, n-heptyl, isoheptyl, n-octyl or isooctyl, $C_2$–$C_{20}$-alkenyl, preferably $C_1$–$C_{12}$-alkenyl, particularly preferably $C_2$–$C_8$-alkenyl, such as vinyl or allyl, $C_2$–$C_{20}$-alkynyl, preferably $C_2$–$C_8$-alkynyl, in particular $C_2H$ or propargyl, $C_3$–$C_{20}$-cycloalkyl, preferably $C_3$–$C_{12}$-cycloalkyl, particularly preferably $C_5$–$C_8$-cycloalkyl, such as cyclopentyl, cyclohexyl, cycloheptyl or cyclooctyl, $C_4$–$C_{20}$-alkylcycloalkyl, preferably $C_4$–$C_{12}$-alkylcycloalkyl, particularly preferably $C_5$–$C_{10}$-alkylcycloalkyl, $C_4$–$C_{20}$-cycloalkylalkyl, preferably $C_4$–$C_{12}$-cycloalkylalkyl, particularly preferably $C_5$–$C_{10}$-cycloalkylalkyl, aryl, such as phenyl, 1-naphthyl or 2-naphthyl, preferably phenyl, $C_7$–$C_{20}$-alkylaryl, preferably $C_7$–$C_{16}$-alkylaryl, particularly preferably $C_7$–$C_{12}$-alkylphenyl, such as 2-methylphenyl, 3-methylphenyl, 4-methylphenyl, 2-ethylphenyl, 3-ethylphenyl or 4-ethylphenyl, or $C_7$–$C_{20}$-aralkyl, preferably $C_7$–$C_{16}$-aralkyl, particularly preferably $C_7$–$C_{12}$-phenalkyl, such as phenylmethyl, 1-phenylethyl or 2-phenylethyl, $R^1$ and $R^2$ together are a saturated or unsaturated $C_3$–$C_9$-alkylene chain, preferably —$(CH_2)_4$—, —$(CH_2)_5$—, —$(CH_2)_7$— and —CH=CH—CH=CH—, $R^3$ or $R^5$ is $C_{21}$–$C_{200}$-alkyl, preferably $C_{40}$–$C_{200}$-alkyl, such as polybutyl, polyisobutyl, polypropyl, polyisopropyl or polyethyl, particularly preferably polybutyl or polyisobutyl, or $C_{21}$–$C_{200}$-alkenyl, preferably $C_{40}$–$C_{200}$-alkenyl, particularly preferably $C_{70}$–$C_{170}$-alkenyl, and $R^3$ and $R^5$ together are a $C_2$–$C_{12}$-alkylene chain, preferably a $C_3$–$C_8$-alkylene chain, particularly preferably —$(CH_2)_3$—, —$(CH_2)_4$—, —$(CH_2)_5$—, —$(CH_2)_6$— or —$(CH_2)_7$—, in particular —$(CH_2)_3$— or —$(CH_2)_4$—,

EXAMPLES

Catalyst Syntheses

Catalyst A: Na-NU-85

Solution A was prepared from 13.3 g of NaOH and 6.6 g of sodium aluminate in 379 g of water. Solution B was prepared from 78 g of hexamethonium bromide (BrMe$_3$N—(CH$_2$)$_6$—NMe$_3$Br) in 378 g of water. Solution C was prepared from 77 g of Aerosil® 50 in 396 g of water. Solution A was mixed with solution B and added to solution C while stirring. Stirring was continued until a homgeneous gel had formed. The mixture was then transferred to an autoclave and crystallized in the course of 260 hours at 160° C. under autogenous pressure while stirring. The zeolite formed was filtered off and washed, dried for 16 hours at 110° C. and calcined for 16 hours at 500° C. X-Ray powder diffraction indicated NU-85.

Catalyst B: H-NU-85

50 g of catalyst A were stirred with 750 g of a 20% strength NH$_4$Cl solution at 80° C. for 2 hours and then filtered off and washed with 1 liter of water. After further NH$_4$Cl exchange and washing, the zeolite was dried for 2 hours at 120° C. and calcined for 5 hours at 500° C. The entire process was then repeated once again. The powder subjected to the exchange had a residual sodium content of less than 0.005%.

42 g of the zeolite subjected to the exchange were compacted with 28 g of boehmite and 1.4 g of formic acid in a kneader and kneaded for 50 minutes with addition of water (53 ml). 2 mm extrudates were produced in an extruder at a compression pressure of 70 bar and were dried for 4 hours at 120° C. and calcined for 16 hours at 500° C.

Catalyst C: Na-NU-85

Catalyst C was sythesized similarly to catalyst A.

Catalyst D: H-NU-85

Catalyst D was subjected to ion exchange similarly to catalyst B, but using catalyst C as a starting material. 40 g of the zeolite which had been subjected to the exchange were compacted with 27 g of boehmite and 1.5 g of formic acid in a kneader and kneaded for 40 minutes with addition of water (61 ml). 2 mm extrudates were produced in an extruder at a compression pressure of 40 bar and were dried for 4 hours at 120° C. and calcined for 16 hours at 500° C. The residual sodium content was less than 0.01%.

Catalyst E: H-NU-85

25 g of catalyst D were introduced into a heatable glass tube and 750 g of a 20% strength NH$_4$Cl solution were circulated over said catalyst by means of a pump at 80° C. for 2 hours. Thereafter, 6 l of H$_2$O were passed straight through over the catalyst and the NH$_4$Cl exchange was repeated once again. After being washed with 10 l of water, the zeolite was dried for 4 hours at 120° C. and calcined for 5 hours at 500° C.

Amination Examples

Amination of Isobutene

The experiments were conducted in a tube reactor (internal diameter 6 mm) under isothermal conditions at from 260° to 300° C. and at a pressure of 280 bar, using a mixture of isobutene and ammonia in a molar ratio of 1:15. The reaction products were analyzed in a gas chromatograph. The results with the various catalysts are compiled in Table 1.

TABLE 1

| Catalyst | Temperature [°C.] | tert-Butylamine yield [% by weight] | | | Density [kg/l] |
| --- | --- | --- | --- | --- | --- |
| | | WHSV 0.75 [g/g.h] | WHSV 1.5 [g/g.h] | WHSV 3 [g/g.h] | |
| D | 260 | 22.47 | | | 0.48 |
| D | 270 | 23.36 | 19.42 | 15.40 | 0.48 |
| D | 280 | 20.92 | | 17.78 | 0.48 |
| E | 260 | 16.94 | | | 0.48 |
| E | 270 | 19.03 | 16.43 | 11.77 | 0.48 |
| E | 280 | 19.58 | 17.99 | 14.32 | 0.48 |
| E | 300 | | | 13.30 | 0.48 |

Amination of Cyclohexene 10 g each of catalyst B and cyclohexene were introduced into a 0.3 l stirred autoclave. After the autoclave had been closed, ammonia (30 ml) and 100 bar nitrogen were forced in, the autoclave was heated to the reaction temperature and stirring was carried out for 16 hours. The results are shown in Table 2, the conversion being based on cyclohexene and the selectivity on cyclohexylamine:

TABLE 2

| $NH_3/C_6H_{10}$ [mol/mol] | Temperature [°C.] | Pressure [bar] | Conversion [%] | Selectivity [%] |
|---|---|---|---|---|
| 1.5:1 | 300 | 275 | 4 | 61 |
| 3:1 | 300 | 400 | 5 | 77 |
| 1.5:1 | 280 | 344 | 1 | 67 |

We claim:

1. A process for the preparation of an amine of the formula I

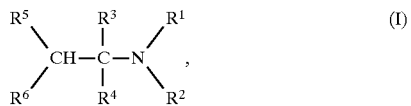

where
$R^1$, $R^2$, $R^3$, $R^4$, $R^5$ and $R^6$: are each hydrogen, $C_1$–$C_{20}$-alkyl, $C_2$–$C_{20}$-alkenyl, $C_2$–$C_{20}$-alkynyl, $C_3$–$C_{20}$-cycloalkyl, $C_4$–$C_{20}$-alkylcycloalkyl, $C_4$–$C_{20}$-cycloalkylalkyl, aryl, $C_7$–$C_{20}$-alkylaryl or $C_7$–$C_{20}$-aralkyl, $R_1$ and $R^2$ together are a saturated or unsaturated $C_3$–$C_9$-alkylene chain and $R^3$ or $R^5$ is $C_{21}$–$C_{200}$-alkyl or $C_{21}$–$C_{200}$-alkenyl or $R^3$ and $R^5$ together are a $C_2$–$C_{12}$-alkylene chain, by reacting an olefin of the general formula II

where $R^3$, $R^4$, $R^5$ and $R^6$ have the abovementioned meanings, with ammonia or a primary or secondary amine of the general formula III

where $R^1$ and $R^2$ have the abovementioned meanings, at from 200° to 350° C. and from 100 to 300 bar in the presence of a heterogeneous catalyst, wherein the heterogeneous catalyst used is an NU-85 zeolite.

2. A process for the preparation of an amine I as claimed in claim 1, wherein the amine I formed is isolated and the unconverted starting materials II and III are recycled.

3. A process for the preparation of an amine as claimed in claim 1, wherein the olefin II used is isobutene, diisobutene, cyclopentene, cyclohexene or polyisobutene.

4. A process for the preparation of an amine as claimed in claim 1, wherein the heterogeneous catalyst used is an NU-85 zeolite in the H form.

5. A process for the preparation of an amine as claimed in claim 1, wherein the heterogeneous catalyst used is an NU-85 zeolite which has been treated with an acid, in particular one selected from the group consisting of hydrochloric acid, hydrofluoric acid, sulfuric acid, phosphoric acid, oxalic acid and mixtures thereof.

6. A process for the preparation of an amine as claimed in claim 1, wherein the heterogeneous catalyst used is an NU-85 zeolite which has been doped with one or more transition metals.

7. A process for the preparation of an amine as claimed in claim 1, wherein the heterogeneous catalyst used is an NU-85 zeolite which has been doped with one or more rare earth elements.

8. A process for the preparation of an amine as claimed in claim 1, wherein the heterogeneous catalyst used is an NU-85 zeolite in the ammonium form.

9. A process for the preparation of an amine as claimed in claim 1, wherein the heterogeneous catalyst used is an NU-85 zeolite which has been doped with one or more elements selected from the group consisting of the alkali metals, alkaline earth metals or earth metals.

10. A process for the preparation of an amine as claimed in claim 1, wherein the heterogeneous catalyst used is an NU-85 zeolite which has been molded with a binder and calcined at from 200° to 600° C.

11. A process for the preparation of an amine as claimed in claim 1, wherein the heterogeneous catalyst used is a dealuminated or deborated NU-85 zeolite.

* * * * *